United States Patent [19]
Richardson et al.

[11] 4,354,984
[45] Oct. 19, 1982

[54] LIQUID LEVEL CONTROLLER FOR A HUMIDIFIER

[75] Inventors: Gerry D. Richardson; Joseph A. Cairo, both of Marietta, Ga.

[73] Assignee: Baxter Travenol Laboratories, Inc., Deerfield, Ill.

[21] Appl. No.: 289,558

[22] Filed: Aug. 3, 1981

[51] Int. Cl.³ .............................................. B01F 3/04
[52] U.S. Cl. ...................................... 261/66; 73/293; 128/200.11; 128/204.13; 137/392; 248/67.7; 248/74 R; 251/7; 261/135; 261/142; 261/154; 261/DIG. 65; 422/106; 422/117; 422/119; 422/125
[58] Field of Search ....................... 261/26, 27, 66, 68, 261/135, 142, 153, 154, DIG. 17, DIG. 65; 73/293, 327; 251/7, 10; 137/392; 248/67.7, 74 R, 74 A, 83; 422/106, 117, 119, 125; 128/200.11, 203.26, 203.27, 205.23, 204.13

[56] References Cited

U.S. PATENT DOCUMENTS

| | | | |
|---|---|---|---|
| 776,695 | 12/1904 | Schwarz et al. | 248/74 R |
| 2,471,623 | 5/1949 | Hubbell | 251/7 X |
| 2,889,848 | 6/1959 | Redmer | 251/7 X |
| 3,419,008 | 12/1968 | Plishner | 251/7 X |
| 3,512,763 | 5/1970 | Winton | 261/66 X |
| 4,267,994 | 5/1981 | Lynch et al. | 248/74 R X |
| 4,303,601 | 12/1981 | Grimm et al. | 261/DIG. 65 |
| 4,305,403 | 12/1981 | Dunn | 251/7 X |

FOREIGN PATENT DOCUMENTS 142462 6/1980 Fed. Rep. of Germany ......... 251/7

*Primary Examiner*—Richard L. Chiesa
*Attorney, Agent, or Firm*—Paul C. Flattery; John A. Caruso; Garretson Ellis

[57] ABSTRACT

Improvements are disclosed in liquid level sensing apparatus having a liquid replenishment line so that as liquid is expended more may be added to keep the liquid at a desired predetermined level. The apparatus is contemplated for use in the humidification of gases, particularly for the administration of oxygen and the like to a patient.

15 Claims, 12 Drawing Figures

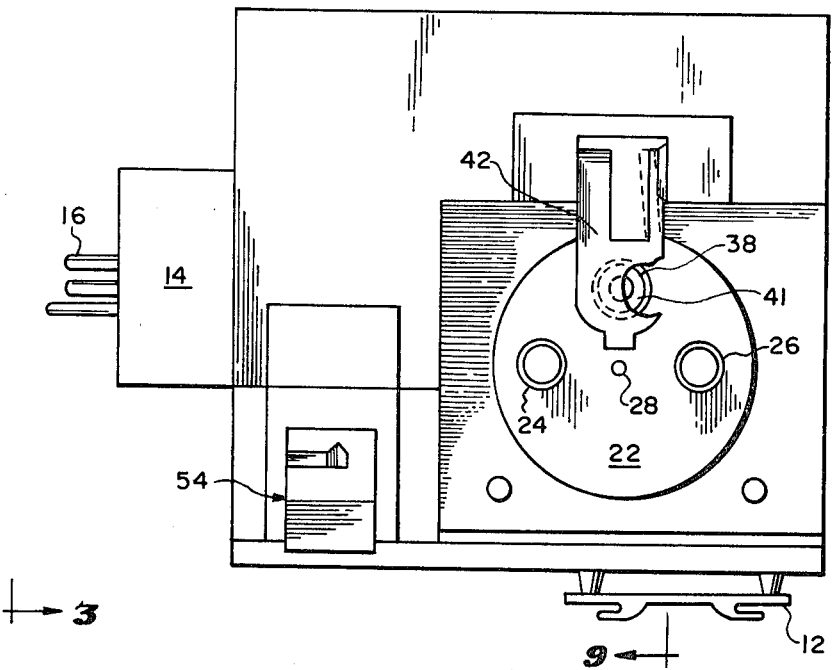
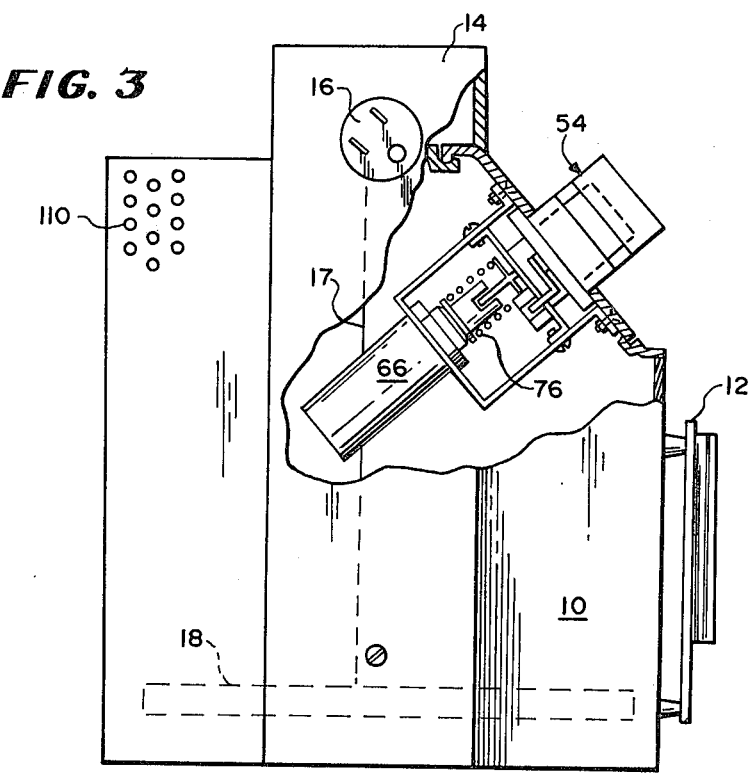

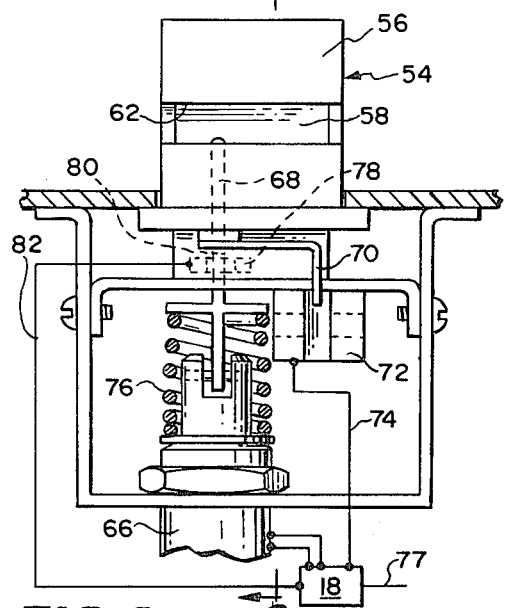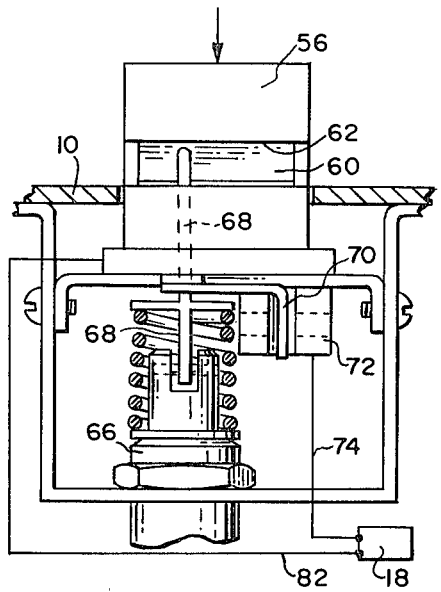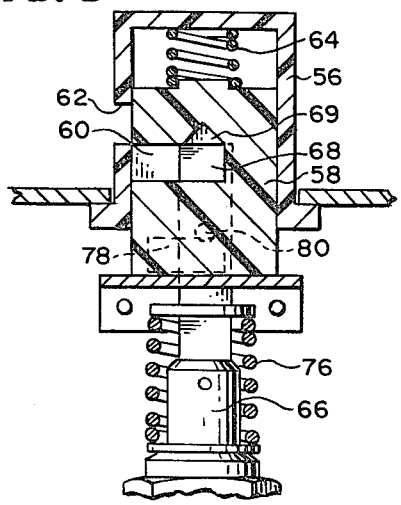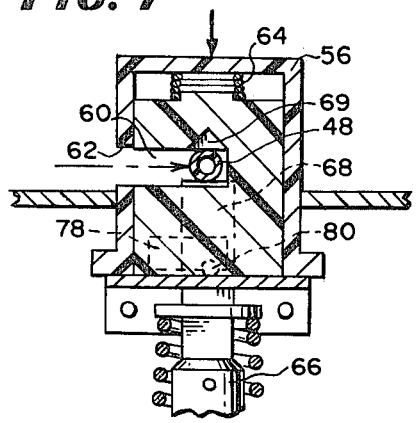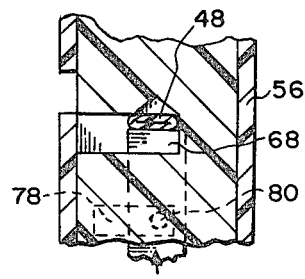

LIQUID LEVEL CONTROLLER FOR A HUMIDIFIER

TECHNICAL FIELD

Humidification devices are desirably used to humidify oxygen gas being administered to a patient. The gas is extremely dry in the form that comes out of its pressurized container.

The need for humidification of the oxygen gas may last for days or longer. Accordingly, it is desirable for the humidification device to be capable of maintaining a water level which provides generally optimum humidification conditions to the system, with apparatus being provided for the automatic replenishment of the water level with only minimal attention by a nurse.

DESCRIPTION OF PRIOR ART

In the Grimm et al. U.S. Pat. application Ser. No. 135,555, filed Mar. 31, 1980, and now U.S. Pat. No. 4,303,601, a ventilator humidifier is disclosed for gases having an automatic liquid level sensing device coupled with an automatically operated valve allowing added liquid to flow into the system, to maintain liquid at the desired optimum level. A removable canister for the liquid has a gas inlet and a gas outlet as part of the flow line to the breathing apparatus of the patient. A tubular wick inside of the canister soaks up water, which is maintained typically at a relatively low level within the canister so that the circulating gas picks up the water primarily off of the tubular wick. More water may be added, for example from a solution bag of sterile water, through a tube into the canister, the tube passing through a solenoid switch, which pinches the tubing shut to stop flow, and intermittently opens it when a low liquid level is sensed. An optical probe is positioned in the canister so that visible light, or typically infrared radiation, passes down the probe and is reflected from the conical end of the probe in the event that the liquid level is low. A sensor detects the reflected light and actuates the solenoid to open the switch.

In accordance with this invention, improvements are provided to the above liquid level detection system, having features of convenience and safety. First, it is desirable to be able to easily replace canisters, which are generally disposable, so that the device may be adapted for use with another patient with a minimum of delay, or may quickly be equipped with a replacement set when that is required by the patient.

Furthermore, safety means may be provided so that a malfunction cannot take place causing the canister to completely fill with liquid. This could cause liquid to be conveyed to the patient which, in the event of a comatose patient, could be dangerous and even life threatening.

DISCLOSURE OF INVENTION

In accordance with this invention a liquid level sensing device, particularly for the humidification of oxygen gas being administered to a patient, is provided for detecting the liquid level in a canister having an optical probe therein. A bracket is carried by a frame, with the bracket carrying a light source and a light sensing member for determining liquid level in the canister in conjunction with the probe.

By this invention the bracket defines first and second parallel arms having free ends, and hinge means between the parallel arms and frame to permit rotation of the bracket into and out of probe-engaging relation.

As the result of this, the probe may be removed and replaced, typically along with the canister, while the bracket is out of probe-engaging relation.

Typically, the first arm of the bracket is more flexible than the second arm. Snap-fit means on the first arm are positioned to mate with corresponding snap-fit means on the frame to releasably retain the bracket in a position out of probe-engaging relation. Thus, the bracket may be easily swung upwardly out of the probe-engaging relation, and the canister, typically with its probe, may be inserted and/or removed with ease.

Typically, switch means is positioned to be closed when the bracket is in a rotating position in probe-engaging relation, to permit actuation of an electrical circuit for normal operation of the device. The switch is open when the bracket is in a rotating position out of probe-engaging relation. Alternatively the switch may be respectively opened and closed in the opposite positions of the brackets with the circuit being conventionally and appropriately designed for this circumstance.

The specific circuit governed by the switch may be one of the operating circuits for the sensing device so that a critical portion of the entire device is disabled while the probe is not engaged by the bracket. Alternatively, the electrical circuit may be a simple alarm circuit so that a signal operates, indicating either the engagement or lack of engagement of the probe by the bracket.

The bracket may rotate about a pivot and may carry an arm member affixed to the bracket. The switch member may include a mirror member carried on the arm member, and a nearby stationary light source and photoreceptor. The mirror may be positioned to reflect light from the light source into the photoreceptor when the bracket is in probe-engaging relation and to not reflect light to the photoreceptor when the bracket is in out of probe-engaging relation (or vice versa) for disablement or actuation of an electrical circuit as described above.

It is also desirable for the bracket to carry a sleeve which surrounds the upper end of the optical probe when the bracket is in probe-engaging relation. The sleeve also encloses the light source and the light sensing member. The result of this is to provide masking from ambient light in the room when the bracket is in probe-engaging relation.

It is to be understood by the term "light" that infrared radiation and the like is intended to be included along with visible light, even though such is not necessarily a visible form of radiation.

The second arm can also serve as a conduit for the electrical leads which communicate with the light source and light sensing member. Also the bracket may be spring biased into the probe-engaging position.

The liquid level retention system of this invention also may include a tube clamp assembly which comprises an inner housing defining a first transverse slot for receiving tubing to be clamped. A hollow outer housing surrounds the inner housing and is manually movable relative to the inner housing between first and second positions. The outer housing defines a second transverse slot positioned in registry with the first slot in the first position but typically not in the second position. Spring means are provided to bias the outer housing into the second position.

Mechanically operated clamp means are provided to releasably clamp the tubing in the first slot. Also means are provided for causing the clamp means to release the tubing from clamping relation when the outer housing is in the first position, and to actuate the clamping relation when the outer housing is in the second position. Thus one can depress the inner housing, causing the first and second transverse slots to be positioned in registry, while the clamp opens. One can slide in tubing which communicates with replenishment liquid for the canister, and then release the outer housing, which spontaneously moves back to the first position, while the clamp means is thus moved to close the tubing.

The means causing the clamp means to release the tubing may include an arm carried by the outer housing plus detection means capable of sensing the arm when the outer housing is in the second position, plus means responsive to the detection means for actuating the clamp means. The detection means may be a photometric cell with the arm moving to interdict a light beam in the cell in the second position, to send a signal for actuating the clamp means.

Added means, controlled by the liquid lvel sensing apparatus described previously, may be provided to independently cause the clamp means to release the tubing upon actuation of the added means. Thus, in the normal operation as the liquid level gets low, the sensing means actuates the added means to open the tube clamp assembly, while the outer housing remains in its first position, so that the liquid level can be maintained by liquid replenishment.

It is also desirable to provide safety overrides to the system so that if the clamp means sticks in an open position due to a mechanical breakdown, unlimited quantities of liquid will not flow into the canister. To this end, the clamp means may define a clamping bar movable between tubing clamping and open positions. The clamping bar defines an aperture, and detection means, particularly photometric detection means, may be positioned to sense the aperture in one position of the clamping bar more than in the other position, as an indicator of the clamping bar position. For example, a photometric detector can sense the presence of the aperture when a light beam can pass through the aperture from a light emitter into the sensor portion of the detector, while the bar is in one position. In another bar position, no light beam will pass through the aperture to the sensor.

Extra means are then provided, responsive to the detection means described above, for actuating the solenoid to override the added means to release the tubing described above, to clamp the tubing in the event the tubing remains open for a predetermined time. Thus, by conventional electronic circuitry a timer can be provided so that the extra means will be actuated if the mechanically operated clamp opens the tubing for a period in excess of, for example 18 seconds. At the same time an alarm may be tripped when the extra means is actuated, while the extra means closes the tubing, to prevent in all circumstances the overfilling of the canister with liquid. The above alarm also will serve as an indication that the liquid source has been exhausted and needs replacement.

BRIEF DESCRIPTION OF THE DRAWINGS

In the drawings,

FIG. 2 is a plan view of the apparatus of FIG. 1, with a portion of the bracket broken away.

FIG. 3 is an elevational view, with portions broken away of the apparatus of FIG. 1.

FIG. 4 is a detailed fragmentary elevational view, with portions broken away, of the tubing clamp assembly shown in FIG. 1.

FIG. 5 is a similar detailed, fragmentary elevational view of the tubing clamp assembly of FIG. 4 shown in another position.

FIG. 6 is a sectional view taken along lines 6—6 of FIG. 4.

FIG. 7 is a corresponding sectional view with respect to FIG. 5.

FIG. 8 is a detailed sectional view similar to FIG. 7 but showing the tubing therein in clamped condition.

DESCRIPTION OF THE SPECIFIC EMBODIMENT

Figure 1:
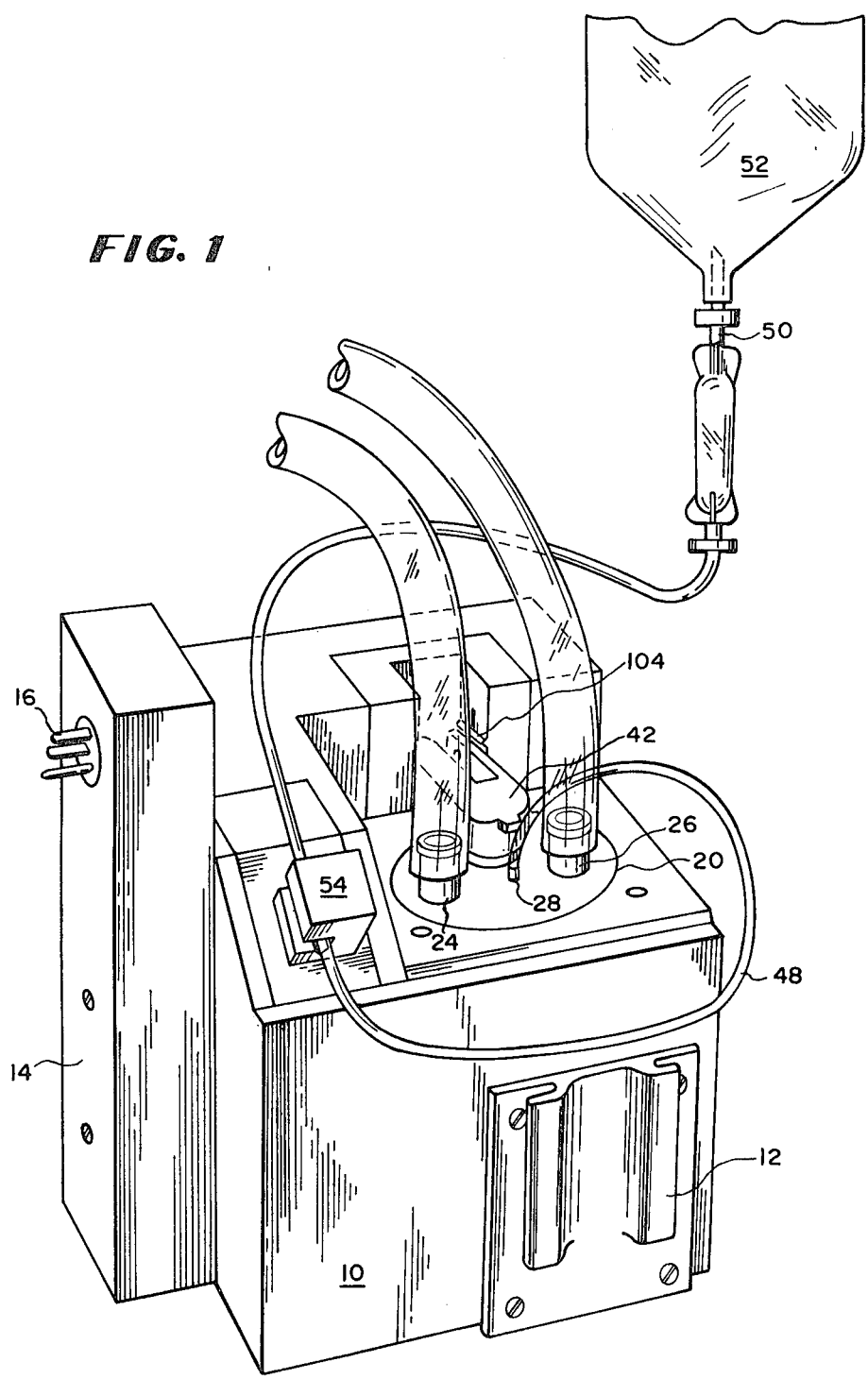
FIG. 1 is a perspective view of a gas humidification apparatus for oxygen inhalation therapy, utilizing the invention of this application.

Referring to FIGS. 1-3, a humidifier in accordance with this invention is disclosed. The humidifier comprises a casing 10 and a hanging bracket 12 so that it can be hung on an IV pole, a wall bracket, or the like. Auxiliary power cord channel 14 basically serves as a rigid extension cord, conveying electrical power by means of conventional wire 17 within channel 14, which communicates between plug 16 and the electronic system 18 of the apparatus, which typically may be in the bottom or side of casing 10 and may comprise one or more printed circuit boards, for example.

Figure 9:
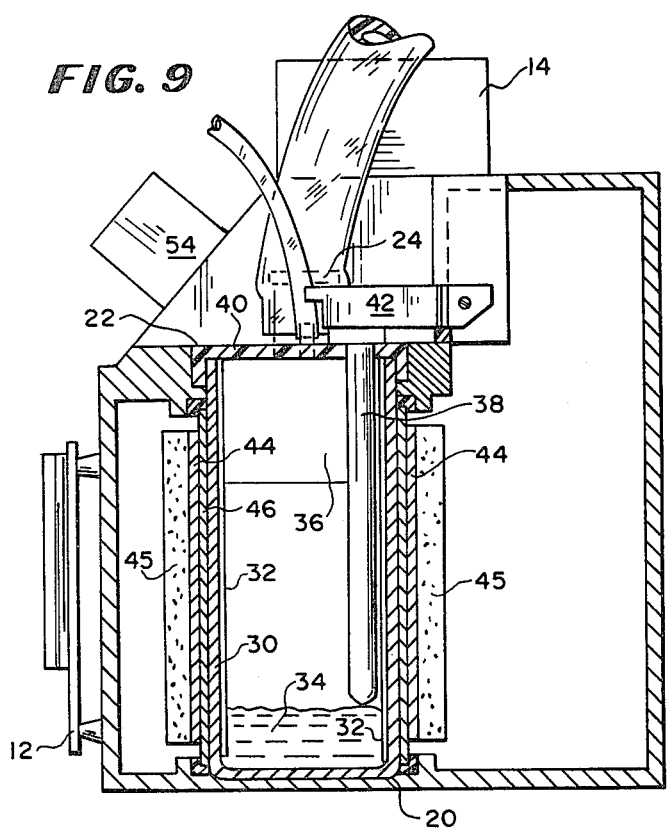
FIG. 9 is a longitudinal sectional view of the apparatus of FIG. 1.

Housing 10 includes a well 20, which is shown to hold a removable canister 22, having oxygen inlet and outlet ports 24, 26 and a water inlet port 28, and being of a design generally shown in FIG. 9 and described in detail in the previously cited patent application.

Specifically, canister 22 includes a thin-walled aluminum can 30 proportioned to fit snugly into well 20. Tubular wick 32 is provided so that liquid 34 in the bottom of the can 30 may be soaked up into wick 32 to provide humidification of gases passing through the can. Baffle member 36 is positioned between inlet 24 and outlet 26 to prevent the shunting of gases from inlet 24 to outlet 26 before humidification has a chance to take place.

Transparent probe 38 is also carried by cover 40 of the canister 22, having a projecting transparent top 41 so that optical or infrared light may pass down the probe 38 and be reflected up again when the level of liquid 34 is too low to be sensed by apparatus within sensing bracket 42, which can engage the top of probe 38.

Strap heater 44 is positioned about the tubular wall 46 that defines well 20 within casing 10, so that the system may be heated for improved humidification. Silicone rubber blanket 45 can insulate heater 44.

As shown in FIG. 1, tubing 48 communicates with liquid entry port 28 at one end and with a conventional spike and drip chamber 50 at the other end, which, in turn, may communicate with a sealed solution container 52 of conventional design, so that sterile water may be provided on a continuous basis to the humidification system. Tubing 48 may pass through tube clamp assembly 54 for control of flow through the tubing.

Referring also to FIG. 4–8, in accordance with this invention tube clamp assembly 54 comprises a hollow outer housing 56 surrounding inner housing 58. Outer housing 56 is manually movable relative to inner housing 58 between first and second positions, the first, depressed position being shown by FIGS. 5 and 7, and the second position being shown in FIGS. 4 and 6.

Inner housing 58 defines a transverse slot 60, while hollow outer housing 56 defines a second transverse slot 62 which is positioned in registry with the first slot 60 in the first position as in FIGS. 5 and 7, but second slot 62 is positioned out of registry with first slot 60 in the second position as shown in FIGS. 4 and 6. A spring 64 is provided to bias the outer housing into the second position of FIGS. 4 and 6.

A solenoid-operated clamp member 66 is provided to clamp tubing in the first slot 60. As shown, clamp member 66 includes a clamping bar 68 which is operated by clamp member 66 to alternatively be open as shown in FIG. 7 to allow flow through tubing 48, or to be closed as in FIG. 8 to obstruct flow through tubing 48.

Means may be provided causing the clamp member 66 to release tubing 48 from clamping relation, as shown in FIG. 7, when the outer housing 56 is in its first position, and also to actuate the clamping relation as shown in FIGS. 4, 6 and 8 when the outer housing 56 is in its second position. This can be specifically accomplished by means of an opaque arm 70 attached to the bottom of outer housing 56. As shown between FIGS. 4 and 5, as the outer housing 56 is depressed to the first position, arm 70 is correspondingly depressed into a conventional photodetector 72 to interrupt a beam of light. This interruption of a beam of light causes a signal to be sent down wire 74 to the electronic circuitry 18 of the appratus. From there a signal may be sent to the mechanically operated clamp means 66 to withdraw bar 68 from its closed position of FIG. 5 into its open position as shown in FIG. 7.

Accordingly, a length of tubing 48 may be inserted through slot 62 into slot 60, the slots being at that moment in registry with each other. Thereafter, when outer housing 56 is released, it springs back into its second position. Angled arm 70 thus rises out of the photodetector 72, causing the signal through line 74 to circuitry 18 to cease, with the result that clamp means 66 permits bar 68 to move forward into the closed position of FIG. 8 once again.

It should be noted that normal position for clamp means 66 is the closed position, with bar 68 being biased into the closed position by spring 76. Thus the solenoid of clamp member 66 may be proportioned to withdraw bar 68 when actuated.

Wall 69 serves as an anvil against which clamping bar 68 can press to collapse tubing 48. On both sides of wall 69 a triangular channel is defined as shown.

Alternatively, other mechanical systems besides a solenoid may be utilized to control bar 68. For example a pneumatic or hydraulic system may be used. Likewise, photodetector 72 can be replaced with other equivalent detector devices. For example, angled arm 70 may be made of a magnetic material, and detector 72 may detect a magnetic flux change created by bringing arm 70 into proximity with the detector. Also other well known alternative detection techniques may be utilized.

An added lead wire 77 may also communicate with circuitry 18 from the photometric read out apparatus, described in greater detail below, which detects by means of probe 38 a low level of liquid 34 in canister member 22. Such an indication of low water level can also cause circuitry 18 to actuate clamp means 66 to open tubing 48, to permit liquid to flow from bag 52 into canister 22 while outer housing remains in its second position.

Additional detection means 78 may be added to the system, to provide a margin of safety so that tubing 48 will not remain open beyond a predetermined length of time under any circumstance. Clamping bar 68 may have an aperture 80 defined therein. As shown in FIG. 8, aperture 80 may be in registry with detector 78 when clamping bar 68 is in the closed position and tubing 48 is installed. Detector cell 78 may be a photometric cell positioned so that a beam of light passing from the light emitter to detector cell 78 to the receiver of cell 78 passes through aperture 80 in this circumstance.

However, as shown in FIG. 4, when tubing 48 is not installed, clamping bar 68 extends too far upwardly so that aperture 80 does not line up properly with detector cell 78, and thus an appropriate not ready signal passes through line 92.

In the circumstance where outer housing 56 is depressed to cause clamping bar 68 to retract in the manner of FIG. 7, or a signal from lead wire 77 retracts bar 68, aperture 80 is too low to be sensed by detector cell 78. Thus in this circumstance, a not ready signal, or else an absence of signal, can also pass through line 82 into the logic circuitry 18. A conventional timer may be activated by the signal from line 82 indicating nonalignment of aperture 80 with detector cell 78, and at the expiration of the time, circuitry 18 deactivates clamp member 66 so that clamping bar 68 is spontaneously driven forward (if not already forward) into the closed position once again. Thus, in the event of a malfunction causing a continuous opening signal to either line 74 or 77, the signal of line 82 and the timer in circuitry 18 causes a fail-safe condition so that liquid cannot pour through tubing 48 in unlimited manner to fill canister member 22. Also an alarm can be set off by the same circumstance which indicates either that a malfunction has taken place or that bag 52 has been drained of liquid.

Circuitry 18 can be adapted to cause the entire system to reset when the condition has been corrected for further normal operation.

Circuitry 18 may be of any conventional design which may be routinely developed by those skilled in the art to accomplish the above functions.

Referring to FIGS. 9–12, the optical probe 38 of canister member 22 is positioned to be connected with bracket 42, which is pivotally attached at pivots 84, 86, to the frame 10. Bracket 42 carries a light source 88, which may be an infrared LED, and a light sensing member 90, which may be a phototransducer. Bracket 42 also carries a sleeve 92 which surrounds light source 88 and light sensing member 90, and also surrounds the top 41 of optical probe 83, to bring them into registry for operation, while at the same time protecting the probe 38 and other components of the liquid level sensing system from stray light.

Figure 12:
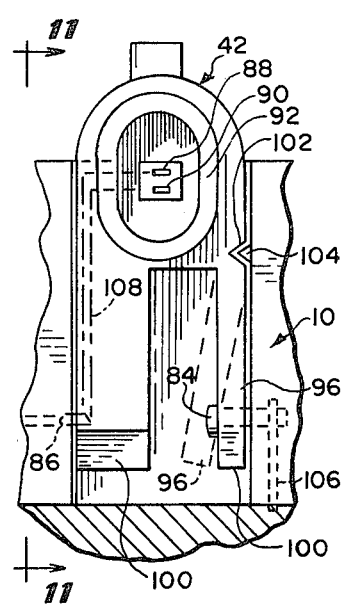
FIG. 12 is a view taken along line 12—12 of FIG. 11.
Figure 10:
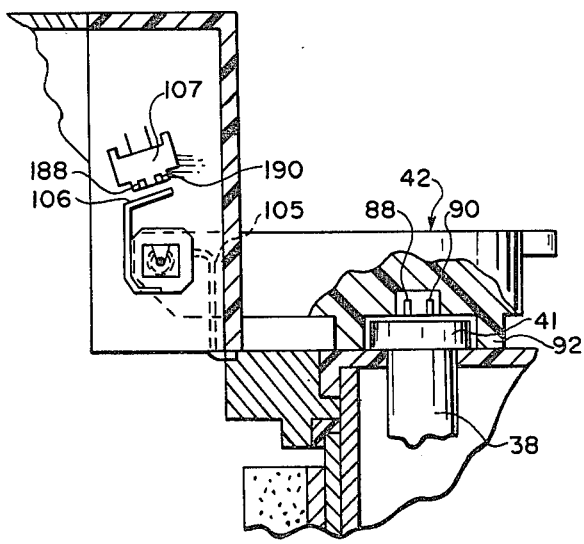
FIG. 10 is an enlarged, detailed view of the structure of FIG. 1, taken partly in section, of the pivotable bracket which moves into and out of probe-engaging relation.
Figure 11:
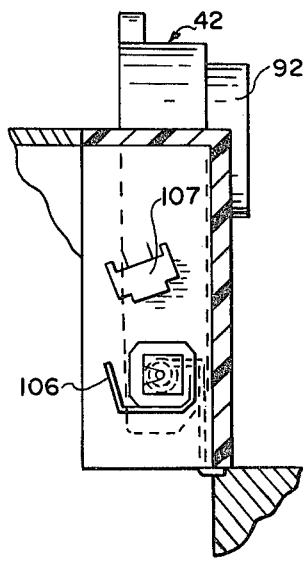
FIG. 11 is a view similar to FIG. 10, but showing the bracket in a different pivotal position.

As shown in FIG. 12, bracket 42 defines first and second parallel arms 96, 98 having free ends 100, being hingedly attached at pivot point 84, 86 as stated above. As shown in FIGS. 10 and 11, arm 42 can rotate into and out of probe-engaging relation so that the canister may be removed and replaced while the bracket is out of probe-engaging relationship as in FIG. 11. First arm 96 is thinner and thus more flexible than the second arm 98 shown by the phantom first arm 96 in FIG. 12, which can bend inwardly as shown as the bracket is rotated, with pivot 84 sliding with it.

Snap-fit means 102 comprises a groove positioned adjacent arm 96, while corresponding snap-fit means 104 in the wall of housing 10 comprises a projection proportioned and positioned to fit into groove 102 when bracket arm 42 is in the vertical position which is out of probe-engaging relation as shown in FIG. 11 to removably retain the bracket in such position. Arm 96 and housing 10 can deform to permit the moving into and out of engaging relation of snap-fit means 102 and 104.

A coil spring 105 may be provided to urge bracket 42 into its horizontal, probe-engaging position as shown in FIGS. 9 and 10, so that the bracket tends to be rotationally pressed into its probe-engaging position, but may be lifted out of probe-engaging position and snapped into a vertically retained position, being retained by snap-fit means 102, 104, as shown in FIG. 12.

One of the pivots 84 of bracket 42 may be a shaft or arm member which is affixed in nonrotating relation with the bracket and also pivotally attached to housing 10. This shaft member 84 may carry a mirror 106.

Photoreceptor cell 107 may contain another LED 188 and a phototransistor 190, similar in overall design to LED 88 and phototransistor 90. Accordingly, when bracket 42 is in the probe-engaging position as shown in FIG. 10, mirror member 106 may be in a position to reflect light from LED 188 to phototransistor 190. Thus cell 107, which operates as a switch, may be part of an alarm of safety indication circuit which indicates in some audible or visible manner the fact that the system is ready to operate when in the position of FIG. 10.

However, when bracket member 42 is in its vertically retained position, out of probe-engaging position, as in FIG. 11, mirror member 106 moves away from member 107 so that light from LED 188 is not reflected into phototransistor 190. This can be used as an indication by cell 107 to electronic system 18 that the overall apparatus is not ready to operate. Alternatively, a portion of the electronics system may be disabled as long as phototransistor 190 is not sensing light so that it cannot operate when bracket 52 is out of probe-engaging relation.

Electrical leads 108 communicate with the light source 88 and light sensing member 90, such leads 108 extending to a power source, typically through circuitry 18, through the second arm 98 of the bracket 42.

Cooling vents 110 are provided in the housing to avoid overheating of the electronics in the interior.

Accordingly, the resulting humidification system automatically provides humidification of gas for a patient, while automatically maintaining the desired level of liquid 34 in the disposable canister member 22 which is placed in the well or aperture 90 of the hardware of the system carried within casing 10. Liquid is passed through line 48 in an automatic manner to maintain the level of liquid 34 in its desired place, while safety systems are provided to prevent overfilling of the canister with liquid. The canister member 22 is easily installed and removed by the simple rotation of bracket 42 out of the way, and safety systems are provided to assure that the system does not operate without the bracket 42 being in a position to detect the liquid level.

The above has been offered for illustrative purposes only, and is not intended to limit the scope of the invention of this application, which is as defined in the claims below.

That which is claimed is:

1. A tube clamp assembly which comprises:
   an inner housing defining a first transverse slot for receiving tubing to be clamped;
   a hollow outer housing surrounding said inner housing and manually movable relative to said inner housing between first and second positions, said outer housing defining a second transverse slot positioned in registry with the first slot in the first position, and spring means to bias said outer housing into the second position;
   clamp means positioned to releasably clamp tubing in said first slot; and
   means causing said clamp to so release said tubing from clamping relation when said outer housing is in the first position and to actuate said clamping relation when the outer housing is in the second position.

2. The tube clamp assembly of claim 1 in which added means is provided to independently cause said clamp means to so release said tubing upon actuation of said added means.

3. The tube clamp assembly of claim 2 in which said clamp means defines a clamping bar movable between tubing clamping and open positions, said bar defining an aperture, first detection means positioned to sense said aperture in one position of said clamping bar more than in the other positions an indicator of the clamping bar position, and extra means responsive to the first detection means for actuating said clamp means to override said added means to clamp said tubing in the event the clamp means remains open for more than a predetermined time.

4. The tube clamp assembly of claim 3 in which said detection means is a photometric cell.

5. The tube clamp assembly of claim 4 in which said tubing releasing means includes an arm carried by said outer housing, second detection means capable of sensing said arm when the outer housing is in the first position, and means responsive to the detection means for actuating the clamp means.

6. The tube clamp assembly of claim 5 in which said second detection means is a photometric cell, and said arm moves to interdict a light beam in said cell in the first position.

7. The tube clamp assembly of claim 1 in which said tubing releasing means includes an arm carried by said outer housing, detection means capable of sensing said arm when the outer housing is in the first position, and means responsive to the detection means for actuating the clamp means.

8. The tube clamp assembly of claim 7 in which said detection means is a photometric cell and said arm moves to interdict a light beam in said cell in the second position.

9. In a humidifier for oxygen gas and the like to be administered to a patient for respiratory therapy, a liquid level sensing device for detecting a liquid level in a canister having an optical probe therein, said sensing device comprising a bracket carried by a frame, said brakcet carrying a light source and a light sensing member for determining liquid level in the canister in conjunction with said probe, and a tube clamp for controlling the flow of replacement liquid to the canister mounted in the humidifier, the improvement comprising, in combination:

said bracket defining first and second parallel arms having free ends, hinge means between the parallel arms and frame to permit rotation of said bracket into and out of probe-engaging relation, whereby the canister may be removed and replaced while the bracket is out of probe-engaging relation, the first arm of said bracket being more flexible than the second arm, and snap-fit means adjacent said first arm positioned to mate with corresponding snap-fit means on the frame, to releasably retain said bracket in a position out of probe-engaging relation;

said tube clamp assembly comprising an inner housing defining a first transverse slot for receiving tubing to be clamped;

a hollow outer housing surrounding the inner housing and manually movable relative to said inner housing between said first and second positions, said outer housing defining a second transverse slot positioned in registry with the first slot in the first position, and spring means to bias said outer housing into the second position;

clamp means positioned to releasably clamp tubing in said first slot; and means causing said clamp means to so release said tubing from clamping relation when said outer housing is in the first position and to actuate said clamping relation when the outer housing is in the second position.

10. The tube clamp assembly of claim 9 in which added means is provided to independently cause the clamp means to so release said tubing upon actuation of said added means.

11. The tube clamp assembly of claim 10 in which said clamp means defines a clamping bar movable between tube clamping and open positions, said bar defining an aperture, detection means positioned to sense said aperture in one position of said clamping bar more than in the other position as an indicator of the clamping bar position, and extra means responsive to the detection means for actuating said clamp means to override said added means, to clamp said tubing in the event the tubing remains open for more than a predetermined time.

12. The tube clamp assembly of claim 11 in which said tubing releasing means includes an arm carried by said outer housing, added detection means capable of sensing said arm when the outer housing is in its second position, and means responsive to the detection means for actuating the clamp means.

13. The humidifier of claim 12 in which both said detection means are photometric cells.

14. The humidifier of claim 13 in which said bracket carries sleeve means which surrounds the upper end of said optical probe when the bracket is in probe-engaging relation said bracket containing the light source and light sensing member.

15. The humidifier of claim 14 in which switch means are provided, said switch means being positioned to be closed when said bracket is in a rotating position in probe-engaging relation to permit actuation of an electrical circuit for normal operation of the device, and said switch means is open when said bracket is in a rotating position out of probe-engaging relation.

* * * * *